(12) United States Patent
Ikeuchi

(10) Patent No.: US 9,980,830 B2
(45) Date of Patent: May 29, 2018

(54) WALKING ASSIST DEVICE

(71) Applicant: HONDA MOTOR CO., LTD., Minato-ku, Tokyo (JP)

(72) Inventor: Yasushi Ikeuchi, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 348 days.

(21) Appl. No.: 14/751,743

(22) Filed: Jun. 26, 2015

(65) Prior Publication Data
US 2015/0374513 A1    Dec. 31, 2015

(30) Foreign Application Priority Data

Jun. 30, 2014   (JP) .................. 2014-134547

(51) Int. Cl.
*A63B 24/00*   (2006.01)
*A61F 2/60*    (2006.01)
*A61F 2/68*    (2006.01)
*A61F 5/01*    (2006.01)

(52) U.S. Cl.
CPC .............. *A61F 2/60* (2013.01); *A61F 2/68* (2013.01); *A61F 5/0102* (2013.01); *A61F 2005/0155* (2013.01)

(58) Field of Classification Search
CPC .. A61F 2/60; A61F 2/68; A61F 5/0102; A61F 2005/0155
See application file for complete search history.

(56) References Cited

U.S. PATENT DOCUMENTS

| | | | | |
|---|---|---|---|---|
| 4,872,665 A * | 10/1989 | Chareire | ............. | A61H 1/0237 482/51 |
| 5,476,441 A * | 12/1995 | Durfee | ................. | A61F 5/0102 434/112 |
| 8,002,719 B2 * | 8/2011 | Ashihara | ............... | B25J 9/0006 601/33 |
| 8,353,854 B2 * | 1/2013 | Horst | ................... | A61H 1/0218 318/139 |
| 8,394,044 B2 * | 3/2013 | Ashihara | ............... | A61H 3/008 135/65 |
| 8,801,641 B2 * | 8/2014 | Kazerooni | ............ | A61H 3/008 128/898 |
| 8,876,741 B2 * | 11/2014 | Matsuoka | .............. | A61H 1/024 601/33 |
| 8,968,223 B2 * | 3/2015 | Ikeuchi | .................. | A61H 3/008 601/23 |
| 9,351,855 B2 * | 5/2016 | Swift | ........................ | A61F 2/68 |
| 9,407,125 B2 * | 8/2016 | Shepertycky | ........ | H02K 7/1861 |
| 9,610,208 B2 * | 4/2017 | Kazerooni | ............ | B25J 9/0006 |
| 9,687,408 B2 * | 6/2017 | Nagasaka | ................ | A61H 3/00 |

FOREIGN PATENT DOCUMENTS

JP   2007-000616 A   1/2007

* cited by examiner

*Primary Examiner* — Glenn Richman
(74) *Attorney, Agent, or Firm* — Carrier Blackman & Associates, P.C.; William D. Blackman; Joseph P. Carrier

(57) ABSTRACT

Provided is a walking assist device independent of a deviation of a bending/stretching state between user's legs and applying a force to a user in a direction intended by the user. The walking assist device performs control so that the larger the deviation of a value of a bending/stretching state variable representing the bending/stretching state of each of a pair of right and left legs of a user P is, the larger the deviation between the assist forces Fr and Fl acting on the user P from each of the leg links 2 is.

3 Claims, 7 Drawing Sheets

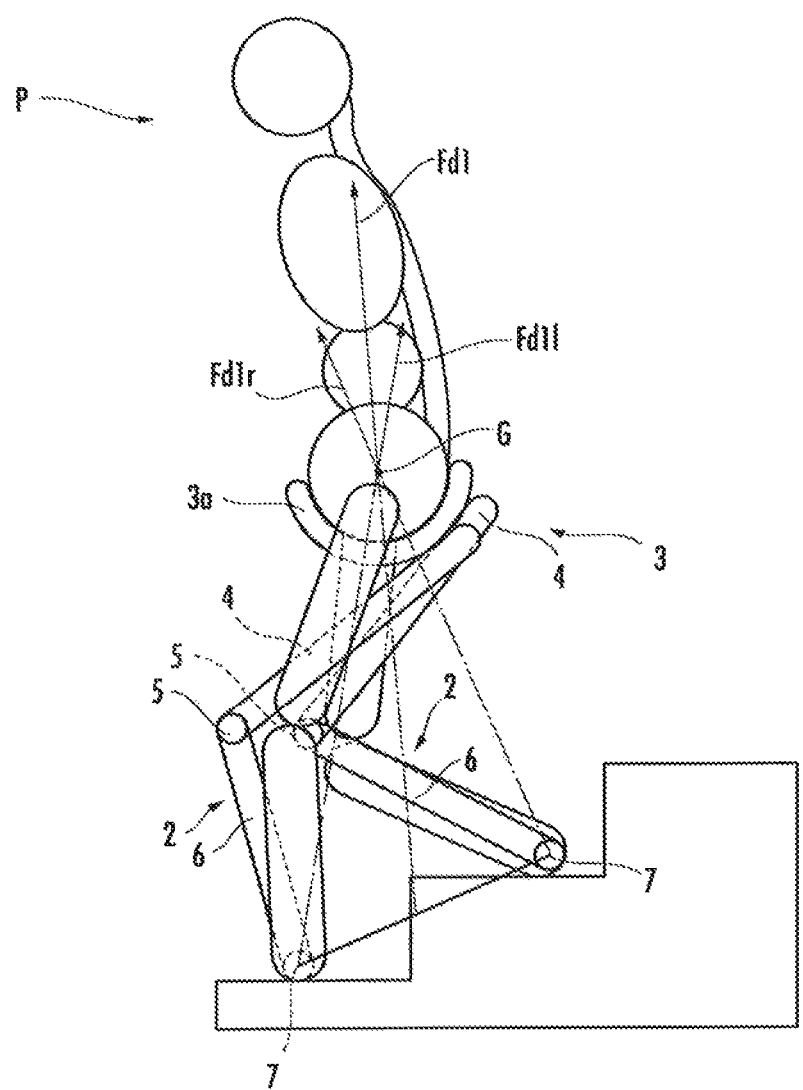

WALKING ASSIST DEVICE

BACKGROUND OF THE INVENTION

Field of the Invention

The present invention relates to a walking assist device which assists a user in walking.

Description of the Related Art

Conventionally, there has been known a walking assist device which assists a person (hereinafter, referred to as "user") in walking who has difficulty in walking due to muscle weakness or the like (for example, refer to Japanese Patent Application Laid-Open No. 2007-000616).

This walking assist device includes a seating portion where the user sits, a pair of right and left leg links swingably connected to the seating portion, and two actuators provided in the leg links, respectively. The leg links each have a thigh frame, a crus frame, and a joint connecting these frames.

The walking assist device having the above configuration drives the joint connecting the frames by using the actuator to cause a force supporting a part of the weight of the user (hereinafter, referred to as "assist force") to act on the trunk of the user from each leg link, thereby reducing the burden on the user's legs during walking to assist the user in walking.

The magnitude of the assist force acting on the user from each leg link is determined by distributing a target assist force necessary for assisting the user in walking according to a ratio between the right-leg side treading force and the left-leg side treading force of the user.

If the leg link is fixed to each user's leg as in the walking assist device described in Japanese Patent Application Laid-Open No. 2007-000616, however, a difference occurs in a bending/stretching state (a bending/stretching state variable) between the user's legs in a situation where the user ascends or descends a slope or stairs. Accordingly, if the assist forces are controlled only based on a ratio between the right-leg side treading force and the left-leg side treading force of the user, there has been a possibility that a force is applied to the user in a direction not intended by the user.

For example, as illustrated in FIG. 6, in the conventional walking assist device, the magnitude of an assist force $Fu1r$ from the right-leg side leg link 2 is the same as the magnitude of the assist force $Fu1l$ from the left-leg side leg link 2 if the right and left treading forces of a user P are the same as each other when the user P is in an ascending walking state (for example, a state where the user P is ascending stairs or an uphill). As a result, a resultant force $Fu1$ between the two assist forces $Fu1r$ and $Fu1l$ gets into a force having not only a vertical component, but also a component directed backward of the user in the back-and-forth direction and therefore a force could be applied to the user P as if the user were pulled backward.

Meanwhile, as illustrated in FIG. 7, in the conventional walking assist device, the magnitude of an assist force $Fd1r$ from the right-leg side leg link 2 is the same as the magnitude of the assist force $Fd1l$ from the left-leg side leg link 2 if the right and left treading forces of the user P are the same as each other when the user P is in a descending walking state (for example, a state where the user P is descending stairs or a downhill). As a result, a resultant force $Fd1$ between the two assist forces $Fd1r$ and $Fd1l$ gets into a force having not only a vertical component, but also a component directed forward of the user in the back-and-forth direction and therefore a force could be applied to the user P as if the user were pulled forward.

SUMMARY OF THE INVENTION

The present invention has been provided in view of the above problems. Therefore, it is an object of the present invention to provide a walking assist device independent of a difference in the bending/stretching state between user's legs and applying a force to the user in a direction intended by the user.

According to one aspect of the present invention, there is provided a walking assist device including: a seating portion on which a user sits; a pair of right and left leg links which are fixed to respective predetermined positions of right and left legs of the user and swingably connected to the seating portion in conjunction with motions of the legs; actuators which transmit driving forces to the leg links to cause assist forces to act on the user from the leg links, respectively, through the seating portion; and a control unit which controls the driving forces of the actuators, wherein the control unit performs the control so that larger a deviation of a value of a bending/stretching state variable representing a bending/stretching state of each of the legs therebetween is, larger the deviation between the assist forces acting on the user from the leg links is.

According to the walking assist device of the present invention, in a situation where the user ascends or descends a slope or stairs, assist forces acting on the user through the seating portion from the respective leg links are differentiated with a consideration for a difference in the bending/stretching state (bending/stretching state variable) between the user's right and left legs. Thereby, even in the case of appearance of such a scene that the forces are applied to the user in directions not intended by the user due to a difference in the bending/stretching state between the legs, the forces are reduced and difficult to be applied to the user in the same situation.

Moreover, preferably the walking assist device of the present invention further includes ground sensors which sense the grounding of the right and left feet of the user and the control unit performs the control only in a state where the right and left feet are on the ground.

If the assist forces are controlled in a state where both of the user's feet are not on the ground, a force could be applied to the user in a direction not intended by the user. Accordingly, the assist forces from the leg links are differentiated only in a state where both of the user's feet are on the ground, by which it is more difficult to apply a force to the user in a direction not intended by the user.

Moreover, the walking assist device of the present invention may include treading force sensors which detect right and left treading forces of the user, wherein: the bending/stretching state variable increases as the knee joint of the user extends more; and the control unit performs the control so that the greater the value of the bending/stretching state variable and the treading forces are, the greater the assist forces are.

BRIEF DESCRIPTION OF THE DRAWINGS

FIG. 7 is an explanatory diagram of assist forces acting on the user by the conventional walking assist device in a descending walking state.

DESCRIPTION OF THE PREFERRED EMBODIMENTS

Hereinafter, a walking assist device according to an embodiment of the present invention will be described with reference to accompanying drawings.

First, the configuration of the walking assist device of this embodiment will be described with reference to FIGS. 1 and 2.

Figure 1:
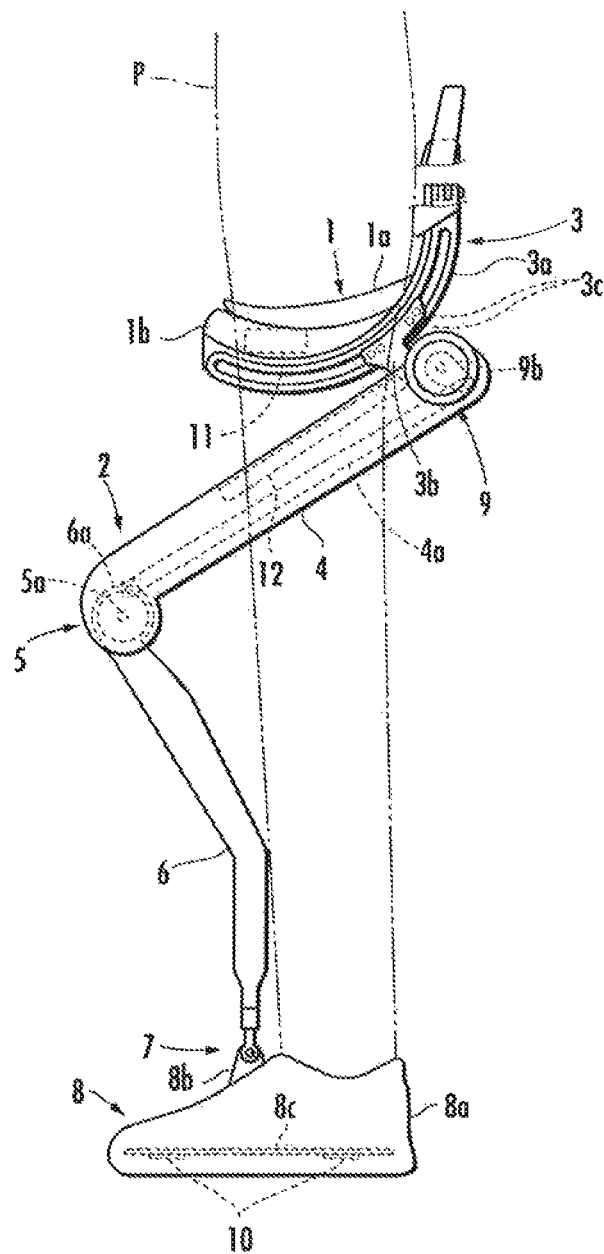
FIG. 1 is a side view illustrating a schematic configuration of a walking assist device according to an embodiment of the present invention.
Figure 2:
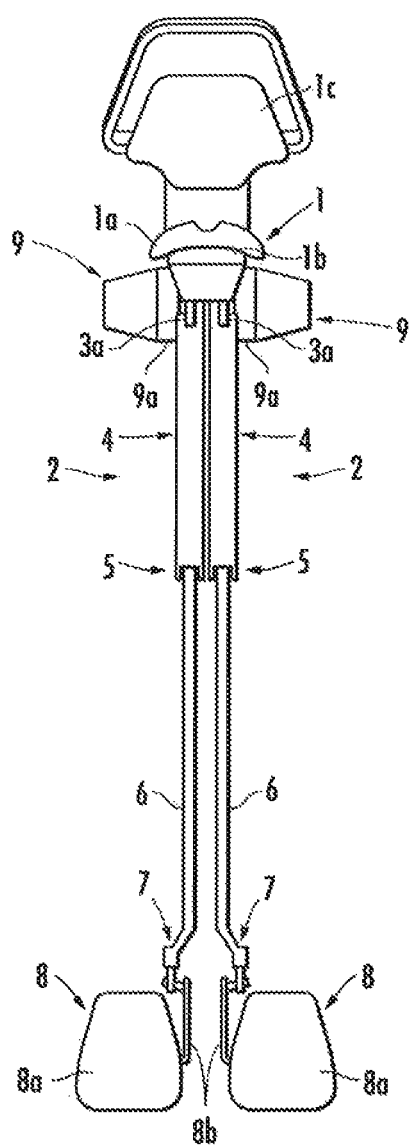
FIG. 2 is a front view of the walking assist device illustrated in FIG. 1.

As illustrated in FIGS. 1 and 2, the walking assist device includes a seating portion 1 where a user P sits astride and a pair of right and left leg links 2 swingably connected to the seating portion 1.

Each leg link 2 is a bendable link mechanism having a thigh frame 4 connected to a first joint 3 provided on the seating portion 1 and a lower limb frame 6 connected to the lower end of the thigh frame 4 through a rotary middle joint 5. Moreover, a foot attachment portion 8 attached to each of the right and left feet of the user P is connected to the lower end of the lower limb frame 6 through a second joint 7.

Furthermore, an actuator 9 for driving the middle joint 5 is mounted on each leg link 2. The actuator 9 rotationally drives the middle joint 5 to drive each leg link 2 in a stretching direction (a direction of pushing up the seating portion 1), thereby generating an assist force.

The assist force generated in each leg link 2 is transmitted to the trunk of the user P through the seating portion 1. As a result, the leg link 2 supports a part of the weight of the user P due to the assist force through the seating portion 1, thereby reducing the load acting on the leg of the user P.

The seating portion 1 includes a saddle-shaped seat 1a where the user P sits, a supporting frame 1b which supports the seat 1a, and a hip cushion 1c mounted on a raised portion at the rear end of the supporting frame 1b raised upward at the backside of the seat 1a.

The first joint 3 includes a guide rail 3a mounted on the raised portion at the rear end of the supporting frame 1b of the seating portion 1, a slider 3b fixed to the top end of the thigh frame 4, and a plurality of rollers 3c which movably engage the slider 3b with the guide rail 3a.

Being connected through the first joint 3, the leg links 2 are swingable in conjunction with the motions of the legs of the user P in a back-and-forth direction with the center of curvature of the guide rail 3a as a swing center (in other words, relative to the seating portion 1). In addition, the swing center of each leg link 2 is the center of curvature of the guide rail 3a.

The actuator 9 includes an electric motor 9a with a speed reducer mounted on the outer side surface of the top end of the thigh frame 4 of each leg link 2 and a driving crank arm 9b on an output shaft of the electric motor 9a.

The driving crank arm 9b is connected to a driven crank arm 6a of the lower limb frame 6 fixed coaxially with the joint axis 5a of the middle joint 5 through the connection link 4a arranged inside the thigh frame 4. Therefore, the lower limb frame 6 swings around the joint axis 5a relative to the thigh frame 4 due to the driving force transmitted from the actuator 9 and thereby the leg link 2 is bent or stretched.

The foot attachment portion 8 has a shoe 8a to be fixed to a foot and a connecting member 8b which is fixed to the shoe 8a and extends in an up-and-down direction. The connecting member 8b is connected to the lower limb frame 6 of each leg link 2 through the second joint 7. Additionally, an insole 8c is provided inside the shoe 8a.

A pair of front and back treading force sensors 10 are mounted on the undersurface of the insole 8c, where the treading force sensors 10 detect loads (treading forces) acting on the metatarsophalangeal joint (MP joint) portion and the heel portion of the foot of the user P. The treading force sensors 10 detect treading forces and also serve as ground sensors which sense whether the feet of the user P are on the ground.

A detection signal from the treading force sensor 10 is input to a controller 11 (control unit). The controller 11 controls the actuator 9 to drive the middle joint 5 on the basis of the swing angles of the first joint 3 and the middle joint 5 and the treading force detected by the treading force sensor 10 in order to generate assist forces acting on the user from the right and left leg links 2.

In this embodiment, the controller 11 is arranged inside the supporting frame 1b of the seating portion 1. Moreover, electric power used for the controller 11 is supplied from a battery 12 arranged inside the thigh frame 4. The controller 11 and the battery 12, however, need not be always housed in the seating portion 1 and the thigh frame 4, respectively, but may be provided outside the walking assist device and the actuator 9 may be controlled via wireless communication or the like.

Subsequently, detailed description will be made on adjustment processing of the assist forces performed by the walking assist device of this embodiment with reference to FIG. 3.

Figure 3:
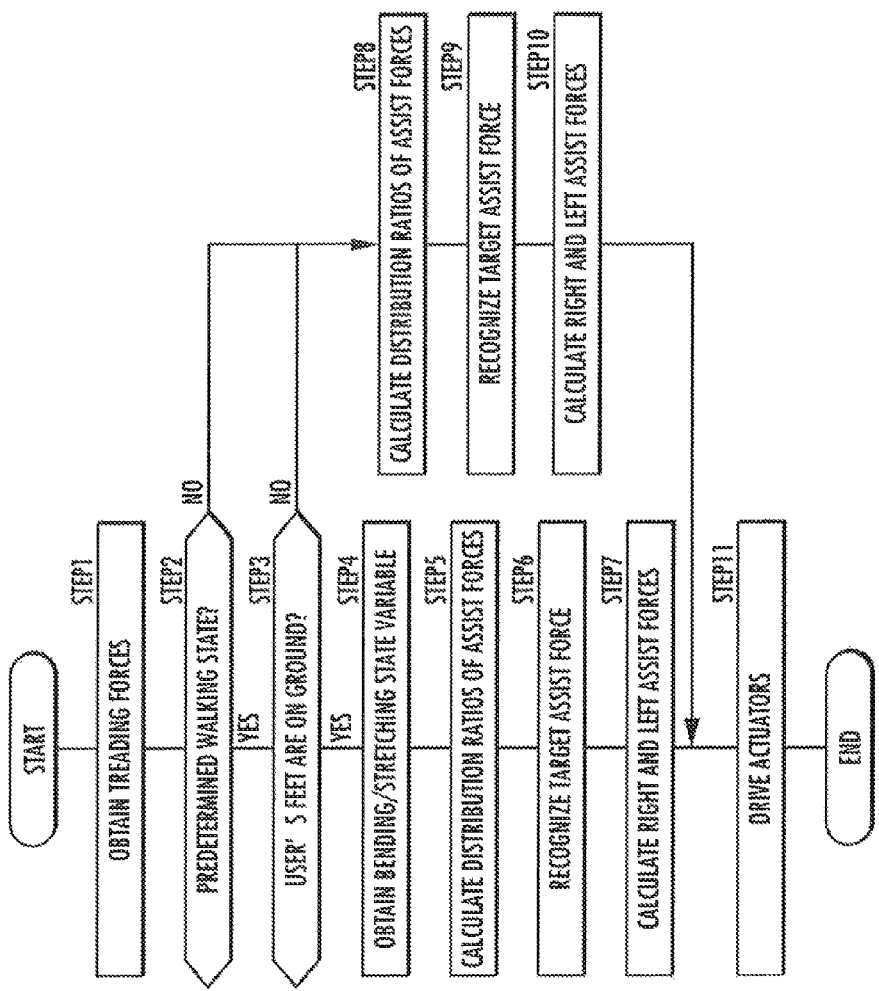
FIG. 3 is a flowchart of processing of adjusting assist forces performed by the walking assist device illustrated in FIG. 1.

First, the controller 11 obtains the right and left treading forces of the user P on the basis of values detected by the treading force sensor 10 (STEP 1 in FIG. 3).

Subsequently, the controller 11 performs the process of determining whether the walking state of the user P is a predetermined walking state (STEP 2 in FIG. 3).

In this embodiment, the controller 11 determines the state to be the predetermined walking state which requires adjustment processing of assist forces using a variable other than the treading forces of the user P if the user P is in an ascending walking state (for example, a state where the user P is ascending stairs or an uphill) and determines the state to be other than the predetermined walking state if the user P is in a level-ground walking state or a descending walking state (for example, a state where the user P is descending stairs or a downhill).

As a method of determining the walking state, for example, there is a method using the timing when each of the right and left feet of the user P touches the ground, the timing when each of the feet is taken off the ground, and a length from the first joint 3 to the second joint 7 of the walking assist device at each timing (hereinafter, the length is referred to as "bending/stretching state variable").

Specifically, first, values detected by the treading force sensor 10 are used to detect the timing when each of the right and left feet of the user P touches the ground, the timing when each foot is taken off the ground, and an angle between the thigh frame 4 and the lower limb frame 6 at each timing.

Then, the bending/stretching state variable is calculated from the angle and the lengths of the thigh frame 4 and the lower limb frame 6. Subsequently, the bending/stretching state variables at the respective timings are compared with each other. If the bending/stretching state variable obtained when one foot is taken off the ground is greater than the bending/stretching state variable obtained at the timing when the foot touches the ground immediately after or before the timing when the foot is taken off the ground by a predetermined value or more as a result of the comparison, it is possible to determine that the user P is in the ascending walking state.

In addition, the method of determining the walking state is not limited to the above method. For example, it is also possible to use a method of determining the walking state on the basis of a result of calculating a moving locus of the second joint 7 from the rotation angles of the first joint 3 and the middle joint 5 and the lengths of the thigh frame 4 and the lower limb frame 6 by measuring changes in the rotation angles in a certain period (refer to Japanese Patent Application Laid-Open No. 2003-116893).

Alternatively, the walking state may be determined on the basis of a result of measuring a moving locus of the second joint 7 relative to the up-and-down direction and the back-and-forth direction in a certain period by using an inertial sensor mounted on the second joint 7.

Furthermore, to determine the walking state, changes in the state of the user P may be measured or the like only for one walking cycle, but preferably the changes are measured or the like for two walking cycles or longer. If measurement or the like is performed for two walking cycles or longer, it is possible to prevent a temporary change in the walking state not requiring adjustment processing of assist forces (for example, a change caused by ascending only one step of an uneven surface or the like) from being determined to be continuous changes in the walking state requiring the adjustment processing (for example, changes caused by ascending stairs).

If it is determined that the user P is in a predetermined walking state (if it is determined that the user P is in an ascending walking state in this embodiment [YES in STEP 2]) as a result of determining the walking state, the controller 11 determines whether the feet of the user P are in the ground-contact state (STEP 3 in FIG. 3).

In the walking assist device of this embodiment, whether the feet of the user P are on the ground is determined on the basis of values detected by the treading force sensors 10 serving as ground sensors.

If it is determined that the user P is in the predetermined walking state (if the user P is in the ascending walking state in this embodiment) and that the feet of the user P are on the ground (YES in STEP 2 and YES in STEP 3) as a result of determining the ground-contact state and the walking state, the controller 11 performs the adjustment processing of the assist forces taking in consideration the bending/stretching state variable of the user P (STEPS 4 to 7 in FIG. 2).

To perform the adjustment processing of the assist forces with consideration of the bending/stretching state variable of the user P, the controller 11 first obtains a bending/stretching state variable in a state where the feet of the user P are on the ground (STEP 4 in FIG. 3).

In this embodiment, a length from the first joint 3 to the second joint 7 is used as the bending/stretching state variable. This bending/stretching state variable has a value able to be geometrically calculated from the rotation angle of the middle joint 5 rotating in conjunction with the motion of the knee joint of the user P and the lengths of the thigh frame 4 and the lower limb frame 6, and the bending/stretching state variable increases as the knee joint of the user P extends more.

In this regard, the bending/stretching state variable in the present invention does not always need to be the length from the first joint 3 to the second joint 7, but only needs to be a value representing the bending/stretching state of each of the right and left legs of the user P. For example, the bending/stretching state variable may be the rotation angle of the middle joint 5 with the upright state of the user P as a reference. In that case, the bending/stretching state variable increases as the knee joint of the user P bends more.

Subsequently, the controller 11 calculates respective distribution ratios Rr and Rl of the assist forces to the right and left leg links 2 on the basis of the treading forces obtained in STEP 1 and the bending/stretching state variable obtained in STEP 4 (STEP 5 in FIG. 3).

In STEP 5 of the walking assist device according to this embodiment, the distribution ratio Rur of the assist force to the right leg link 2 is calculated according to the following expression (1) and the distribution ratio Rul of the assist force to the left leg link 2 is calculated according to the following expression (2):

$$Rur = Ffr \times Lr/(Ffr \times Lr + Ffl \times Ll) \quad (1)$$

$$Rul = Ffl \times Ll/(Ffr \times Lr + Ffl \times Ll) \quad (2)$$

In the above expressions (1) and (2), Ffr is the treading force of the right leg of the user P, Ffl is the treading force of the left leg of the user P, Lr is the bending/stretching state variable of the right-leg side leg link 2, and Ll is the bending/stretching state variable of the left-leg side leg link 2.

As apparent from the above expressions (1) and (2), the controller 11 performs the adjustment processing so that the greater the value of the bending/stretching state variable and the treading force are, the greater the assist force is. Specifically, the controller 11 performs the adjustment processing so that the larger the deviation of the value of the bending/stretching state variable is, the larger the deviation between the assist forces is.

The above calculation method of the distribution ratio, however, is merely illustrative. Any method may be used as long as the method is effective to obtain a distribution ratio which causes the back-and-forth direction component of the resultant force of the assist forces from the right and left leg links 2 to be smaller as described later.

For example, the distribution ratios Rur and Rul of the assist forces may be calculated by using the following expressions (1A) and (2A) without consideration of the treading forces of the user P:

$$Rur = Lr/(Lr + Ll) \quad (1A)$$

$$Rul = Ll/(Lr + Ll) \quad (2A)$$

Subsequently, the controller 11 recognizes a target assist force Fu necessary for supporting a part of the weight of the user P (STEP 6 in FIG. 3).

In this embodiment, the target assist force Fu is recognized by reading data (for example, data related to a correlation between a walking state and a load to be supported in the walking state) previously stored in a memory (not illustrated) and collating the data with the determined walking state.

The target assist recognition method is not limited to the above method, however, and any method may be used as long as the method is effective to recognize an assist force able to support a part of the weight of the user P. For example, the target assist recognition method may be a method of determining the target assist force on the basis of the treading forces obtained while the user is walking by using values detected by the treading force sensor 10.

Subsequently, the controller 11 calculates the assist forces Fur and Ful to be caused to act on the user P from the right and left leg links 2, respectively, on the basis of the distribution ratios calculated in STEP 5 and the target assist force Fu determined in STEP 6 (STEP 7 in FIG. 3).

In STEP 7 of the walking assist device of this embodiment, the assist force Fur from the right leg link 2 is calculated according to the following expression (3) and the assist force Ful from the left leg link 2 is calculated according to the following expression (4):

$$Fur = Fu \times Rur \quad (3)$$

$$Ful = Fu \times Rul \quad (4)$$

Meanwhile, if it is determined that the user P is not in the predetermined walking state (in this embodiment, the user P is determined to be in the level-ground walking state or in the descending walking state [NO in STEP 2]) or that the feet of the user P are not on the ground (NO in STEP 3) as a result of determining the walking state and the ground-contact state, the controller 11 performs the adjustment processing of the assist forces without consideration of the bending/stretching state variable of the user P (STEPS 8 to 10 in FIG. 3), similarly to the conventional walking assist device (See FIG. 7).

In the case of performing adjustment processing of assist forces without consideration of the bending/stretching state variable of the user P, the controller 11 first calculates the distribution ratios $Rd1r$ and $Rd1l$ of the assist forces to the right and left leg links 2 on the basis of only the treading forces obtained in STEP 1 (STEP 8 in FIG. 3).

In STEP 8 of the walking assist device of this embodiment, the distribution ratio $Rd1r$ of the assist force to the right leg link 2 is calculated according to the following expression (5) and the distribution ratio $Rd1l$ of the assist force to the left leg link 2 is calculated according to the following expression (6):

$$Rd1r = Ffr/(Ffr+Ffl) \quad (5)$$

$$Rd1l = Ffl/(Ffr+Ffl) \quad (6)$$

In the above expressions (5) and (6), Ffr is a treading force of the right leg of the user P and Ffl is a treading force of the left leg of the user P.

The above calculation method of the distribution ratio, however, is merely illustrative. Any method may be used as long as the method is effective to obtain a distribution ratio which makes it difficult to apply an excessive force to the user P in the back-and-forth direction in the level-ground walking state or the descending walking state.

Subsequently, the controller 11 recognizes a target assist force Fd1 necessary for supporting a part of the weight of the user P (STEP 9 in FIG. 3).

Then, the controller 11 calculates the assist forces $Fd1r$ and $Fd1l$ to be caused to act on the user P from the right and left leg links 2, respectively, on the basis of the distribution ratios calculated in STEP 8 and the target assist force Fd1 determined in STEP 9 (STEP 10 in FIG. 3).

In STEP 10 of the walking assist device of this embodiment, the assist force $Fd1r$ from the right leg link 2 is calculated according to the following expression (7) and the assist force $Fd1l$ from the left leg link 2 is calculated according to the following expression (8):

$$Fd1r = Fd1 \times Rd1r \quad (7)$$

$$Fd1l = Fd1 \times Rd1l \quad (8)$$

Finally, the controller 11 drives the right and left actuators 9 so as to cause the right and left leg links 2 to apply the assist forces Fur, Ful, $Fd1r$, and $Fd1l$ determined in STEP 7 or 10 and terminates the adjustment processing of the assist forces (STEP 11 in FIG. 3).

Subsequently, the assist forces applied by the walking assist device of this embodiment will be described in detail with reference to FIG. 4.

Figure 4:
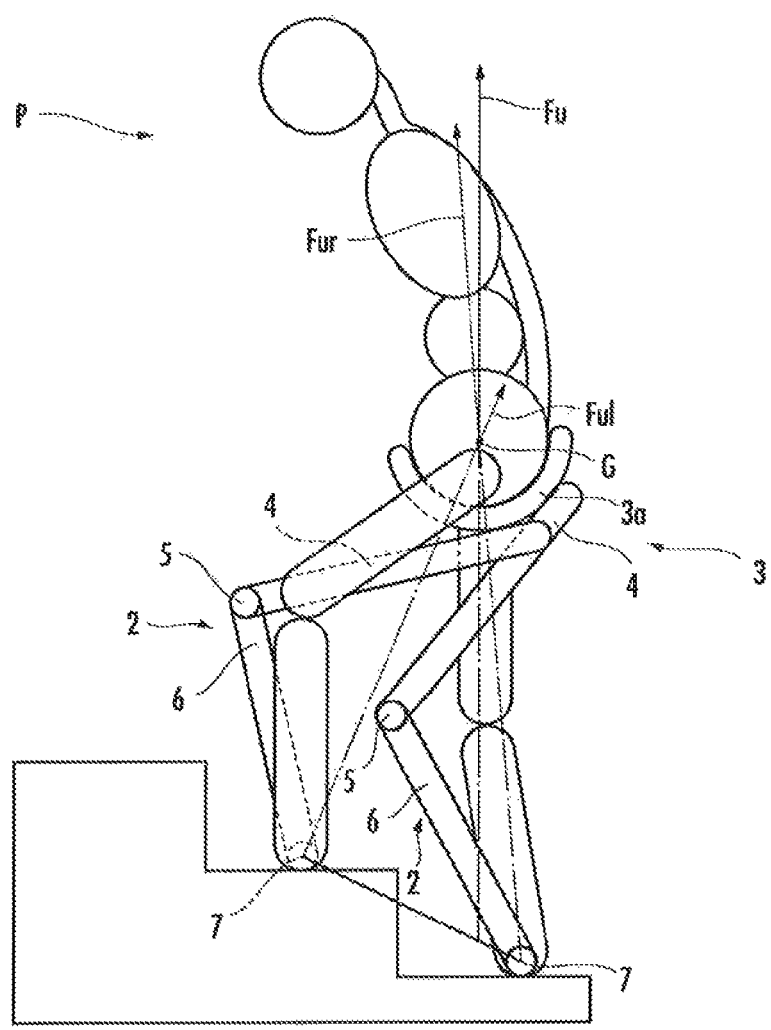
FIG. 4 is an explanatory diagram, of assist forces acting on the user by the walking assist device illustrated in FIG. 1 in an ascending walking state.

When the user P is in the ascending walking state as illustrated in FIG. 4, the step-out forward leg (the left leg in FIG. 4) bends compared to the rearward leg, thereby generating a difference in the bending/stretching state between the right and left legs of the user P. Specifically, the deviation of the value of the bending/stretching state variable is larger than that of the normal walking state, where the bending/stretching state variable indicates the bending/stretching state of each of the right and left legs of the user P.

In this condition, the direction of the assist force Fur from the right-leg side leg link 2 and the direction of the assist force Ful from the left-leg side leg link 2 are directions from the center of rotation of each second joint 7 to the swing center G of each leg link 2.

Furthermore, in the walking assist device of this embodiment, the controller 11 adjusts the assist force Ful from the step-out leg link 2 on the left leg side so as to be small and the assist force Fur from the rearward leg link 2 on the right-leg side so as to be large according to a difference in the bending/stretching state (a deviation of the value of the bending/stretching state variable). In other words, the adjustment processing is performed so that the deviation between the assist forces Fur and Ful is larger than the deviation in the normal walking state.

Figure 6:
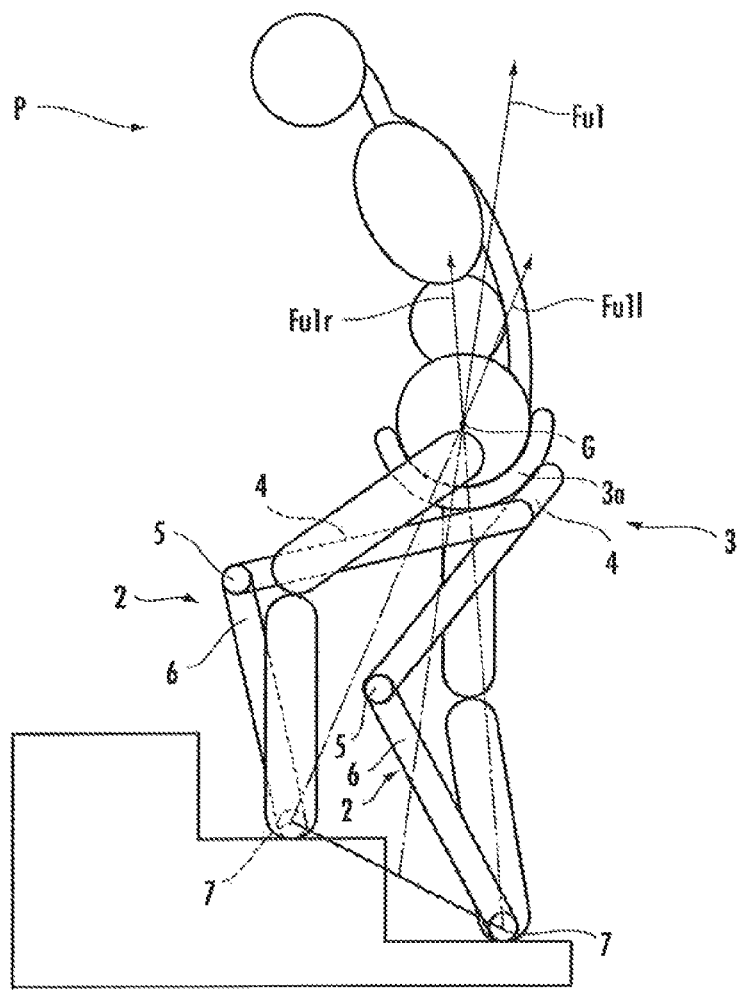
FIG. 6 is an explanatory diagram of assist forces acting on the user by a conventional walking assist device in an ascending walking state.

Therefore, the back-and-forth direction component of the resultant force Fu of the assist forces acting on the user P from the leg links 2 approaches zero (See FIG. 4). Specifically, the resultant force Fu of the assist forces acting on the user P from each of the leg links 2 gets smaller in the back-and-forth direction component in comparison with the conventional walking assist device, thereby reducing the force applied to the user P in the back-and-forth direction (See FIGS. 4 and 6).

Therefore, according to the walking assist device of the present invention, even in the case of a situation where a force in a direction not intended by the user P is applied to the user P due to a difference in the bending/stretching state between the legs, the force is reduced to make it difficult for the force to be applied to the user P.

Although an exemplary embodiment of the present invention has been described hereinabove, the present invention is not limited to only the exemplary embodiment.

For example, in the above embodiment, the controller 11 performs the adjustment processing with consideration of the bending/stretching state variable only in a situation where the user P is ascending stairs. The walking assist device according to the present invention, however, is not limited to the configuration. For example, even if the user is in the level-ground or the descending walking state, the control unit may perform control with consideration of the bending/stretching state variable.

Specifically, for example, also in the descending walking state (for example, a state of descending stairs or a downhill), the control may be performed with consideration of the bending/stretching state variable similarly to the control in the ascending walking state in the above embodiment.

Figure 5:
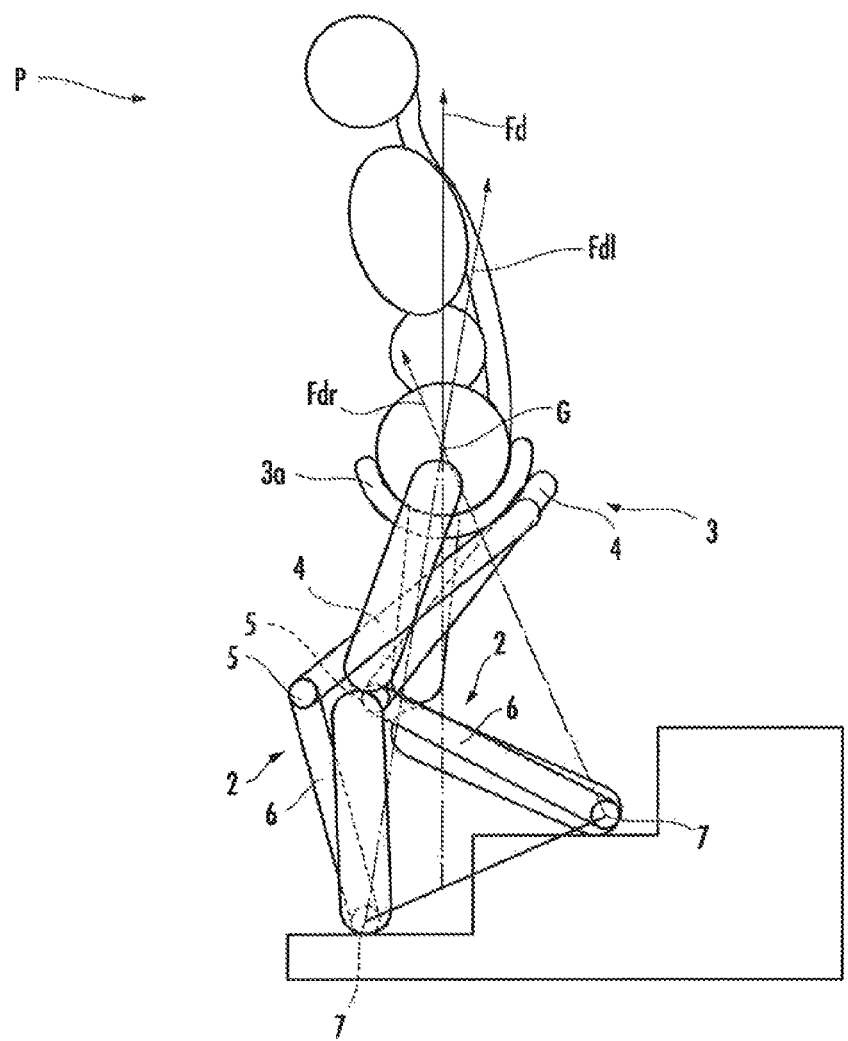
FIG. 5 is an explanatory diagram of assist forces acting on the user by a walking assist device according to a variation of the embodiment of the present invention in a descending walking state.

As illustrated in FIG. 5, in the case of having performed such control the back-and-forth direction component of the resultant force Fd of the assist force Fdr from the right-leg side leg link 2 and the assist force Fdl from the left-leg side leg link 2 approaches zero. Specifically, the resultant force Fd of the assist forces acting on the user P from each of the leg links 2 gets smaller in the back-and-forth direction component in comparison with the conventional walking assist device, thereby reducing the force applied to the user P in the back-and-forth direction (See FIGS. 5 and 7).

As a result, even in the case of a situation where a force in a direction not intended by the user P is applied to the user P due to a difference in the bending/stretching state between the legs when the user P is in the descending walking state, the force is reduced to make it difficult for the force to be applied to the user P.

Moreover, in the above embodiment, the controller 11 performs adjustment processing of assist forces with consideration of the bending/stretching state variable only when determining that the feet of the user P are on the ground. The walking assist device of the present invention, however, is not limited to the configuration. For example, the control by the control unit may be performed on a constant basis during one walking cycle or may be performed only for a certain period of one walking cycle. Furthermore, in the ascending walking state, the control may be performed only when a walker takes a step. Alternatively, the control may be performed only when the deviation of the bending/stretching state variable exceeds a predetermined deviation.

Moreover, in the above embodiment, the controller 11 performs adjustment processing of the assist forces Fur and Ful acting on the user P from the leg links 2 respectively so that the back-and-forth direction component of the resultant force Fu of the assist forces approaches zero, where the assist forces act on the user P from the right and left leg links 2. The control performed by the control unit of the present invention, however, need not be necessarily such adjustment that the resultant force of the assist forces is controlled as described above.

For example, when the user is in the ascending walking state, the resultant force of the assist forces may be controlled so as to be a force pulling the user slightly forward. In contrast, when the user is in the descending walking state, the resultant force of the assist forces may be controlled so as to be a force pulling the user slightly backward.

Moreover, in the above embodiment, the leg link 2 is configured as a bendable link mechanism in which the thigh frame 4 and the lower limb frame 6 are connected via the middle joint 5. The leg link of the present invention, however, is not limited to the configuration. The leg link may have any configuration as long as it is able to bend and stretch according to the user's walking and to generate assist forces. For example, a linear expansion mechanism may be used, instead of the link mechanism.

Furthermore, in the above embodiment, the leg of the user P is fixed to the leg link 2 through the shoe 8a of the foot attachment portion 8 connected to the leg link 2. The walking assist device of the present invention, however, is not limited to the configuration, and any region may be fixed to the leg link 2 as long as the leg link is swingable in conjunction with the motions of the user's leg. For example, the user's thigh or crus may be fixed to the leg link 2.

Moreover, in the above embodiment, each treading force sensor 10 also serves as a ground sensor. The treading force sensor and the ground sensor of the present invention, however, are not limited to the configuration, and any configuration may be used as long as the sensors are able to sense the user's treading force and ground-contact state. For example, the treading force sensor and the ground sensor may be provided as sensors independent of each other. In addition, the installation positions may be set appropriately.

DESCRIPTION OF REFERENCE NUMERALS 1 seating portion
1a seat
1b supporting frame
1c hip cushion
2 leg link
3 first joint
3a guide rail
3b slider
3c roller
4 thigh frame
4a connection link
5 middle joint
5a joint axis
6 lower limb frame
6a driven crank arm
7 second joint
8 foot attachment portion
8a shoe
8b connecting member
8c insole
9 actuator
9a electric motor
9b driving crank arm
10 treading force sensor
11 controller
12 battery
G swing center of leg link 2
P user

What is claimed is:
1. A walking assist device comprising:
a seating portion on which a user sits;
a pair of right and left leg links which are adapted to be fixed to respective predetermined positions of right and left legs of the user, the leg links being swingably connected to the seating portion for movement in conjunction with motions of the legs;
actuators which are configured to transmit driving forces to the leg links to cause assist forces to act on the user from the leg links, respectively, through the seating portion; and
a control unit which recognizes a target assist force and obtains values of bending/stretching state variables which represent bending/stretching states of the right and left leg links to control the driving forces of the actuators,
wherein the control unit calculates respective distribution ratios for the right and left leg links in accordance with the values of the bending/stretching state variables to calculate the respective driving forces for each of the right and left leg links by multiplying the target assist force by the corresponding distribution ratios.
2. The walking assist device according to claim 1, further comprising ground sensors which sense the grounding of right and left feet of the user, wherein the control unit performs the control only in a state where both of the right and left feet are on a ground surface.

3. The walking assist device according to claim 1, further comprising treading force sensors which detect right and left treading forces of the user, wherein:
- each of the bending/stretching state variables is a variable that increases as a corresponding knee joint of the user extends more; and
- the control unit calculates the respective distribution ratios for each of the right and left leg links by multiplying the values of the bending/stretching state variables by the corresponding right and left treading forces.

* * * * *